US012642571B2

(12) United States Patent
Puterbaugh et al.

(10) Patent No.: US 12,642,571 B2
(45) Date of Patent: Jun. 2, 2026

(54) MULTIPLEXED HAND SWITCHES FOR USE WITH ELECTROSURGICAL GENERATORS

(71) Applicant: Covidien LP, Mansfield, MA (US)

(72) Inventors: Lewis R. Puterbaugh, Longmont, CO (US); Mark A. Johnston, Boulder, CO (US)

(73) Assignee: Covidien LP, Mansfield, MA (US)

( * ) Notice: Subject to any disclaimer, the term of this patent is extended or adjusted under 35 U.S.C. 154(b) by 768 days.

(21) Appl. No.: 17/862,541

(22) Filed: Jul. 12, 2022

(65) Prior Publication Data

US 2023/0108257 A1 Apr. 6, 2023

Related U.S. Application Data

(60) Provisional application No. 63/245,213, filed on Sep. 17, 2021.

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/00607* (2013.01); *A61B 2018/00767* (2013.01); *A61B 2018/00875* (2013.01)

(58) Field of Classification Search
CPC .. A61B 2018/0063; A61B 2018/00601; A61B 2018/00607; A61B 2018/00708; A61B 2018/00916; A61B 2018/00922; A61B 18/1206; A61B 18/1445
See application file for complete search history.

(56) References Cited

U.S. PATENT DOCUMENTS

| | | | |
|---|---|---|---|
| 1,787,709 | A | 1/1931 | Charles |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,693,106 | A | 11/1954 | Henry |
| 2,827,056 | A | 3/1958 | John |

(Continued)

FOREIGN PATENT DOCUMENTS

| | | |
|---|---|---|
| DE | 179607 C | 11/1906 |
| DE | 390937 C | 3/1924 |

(Continued)

OTHER PUBLICATIONS

US 6,878,148 B2, 04/2005, Goble et al. (withdrawn)

(Continued)

*Primary Examiner* — Michael F Peffley
*Assistant Examiner* — Samantha M Good

(57) ABSTRACT

An electrosurgical system includes an electrosurgical device including a pair of opposing jaw members movable between an open jaw position and a closed jaw position, a main switch, a button configured to actuate the main switch, and a secondary switch configured to actuate based on the thickness of the grasped tissue. The system also includes an electrosurgical generator coupled to the electrosurgical device, the electrosurgical generator is configured to generate an electrosurgical output in response to actuation of the main switch and the secondary switch.

10 Claims, 6 Drawing Sheets

(56)                 References Cited

U.S. PATENT DOCUMENTS

| | | | |
|---|---|---|---|
| 2,849,611 A | 8/1958 | Adams |
| 2,883,198 A | 4/1959 | Natsuo |
| 3,001,132 A | 9/1961 | Howard |
| 3,058,470 A | 10/1962 | Ernst et al. |
| 3,089,496 A | 5/1963 | John |
| 3,154,365 A | 10/1964 | Crimmins |
| 3,163,165 A | 12/1964 | Humio |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Gulik |
| 3,562,623 A | 2/1971 | Farnsworth |
| 3,571,644 A | 3/1971 | Jakoubovitch |
| 3,589,363 A | 6/1971 | Banko et al. |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,118,700 A * | 10/1978 | Lenihan ............... G08B 25/018 |
| | | 323/354 |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Fastenmeier et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | Mcgreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |

(56) References Cited

U.S. PATENT DOCUMENTS

| | | |
|---|---|---|
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes et al. |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,057,105 A | 10/1991 | Malone et al. |
| 5,067,953 A | 11/1991 | Feucht |
| 5,075,839 A | 12/1991 | Fisher et al. |
| 5,078,153 A | 1/1992 | Nordlander et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | Mcelhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan |
| 5,201,900 A | 4/1993 | Nardella |
| 5,207,691 A | 5/1993 | Nardella |
| 5,216,338 A | 6/1993 | Wilson |
| 5,230,623 A | 7/1993 | Guthrie et al. |
| 5,233,515 A | 8/1993 | Cosman |
| 5,234,427 A | 8/1993 | Ohtomo et al. |
| 5,244,462 A | 9/1993 | Delahuerga et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,269,780 A | 12/1993 | Roos |
| 5,271,413 A | 12/1993 | Dalamagas et al. |
| 5,281,213 A | 1/1994 | Milder et al. |
| 5,282,840 A | 2/1994 | Hudrlik |
| 5,295,857 A | 3/1994 | Toly |
| 5,300,068 A | 4/1994 | Rosar et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,876 A | 1/1995 | Nardella |
| 5,385,148 A | 1/1995 | Lesh et al. |
| 5,396,194 A | 3/1995 | Williamson et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Langley et al. |
| 5,422,567 A | 6/1995 | Matsunaga |
| 5,422,926 A | 6/1995 | Smith et al. |
| 5,423,809 A | 6/1995 | Klicek |
| 5,423,810 A | 6/1995 | Goble et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen et al. |
| 5,445,638 A | 8/1995 | Rydell et al. |
| 5,448,466 A | 9/1995 | Erckert |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,498,261 A | 3/1996 | Strul |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |

(56)                References Cited

U.S. PATENT DOCUMENTS

| | | | |
|---|---|---|---|
| 5,541,376 A | 7/1996 | Ladtkow et al. |
| 5,542,916 A | 8/1996 | Hirsch et al. |
| 5,545,161 A | 8/1996 | Imran |
| 5,554,172 A | 9/1996 | Horner et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Struijk et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | Mcmahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,927 A | 12/1997 | Imran et al. |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,165 A | 6/1998 | Gentelia et al. |
| 5,769,847 A | 6/1998 | Panescu et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,990 A | 11/1998 | Li |
| 5,843,019 A | 12/1998 | Eggers et al. |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,739 A | 2/1999 | Lindenmeier et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | Baudino et al. |
| 5,931,835 A | 8/1999 | Mackey |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | North et al. |
| 5,944,553 A | 8/1999 | Yasui et al. |
| 5,948,007 A | 9/1999 | Hall et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | Mccary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Cosman et al. |
| 5,999,848 A | 12/1999 | Gord et al. |
| 6,002,968 A | 12/1999 | Edwards |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,347 A | 2/2000 | Lindenmeier et al. |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,780 A | 5/2000 | Gough et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,089,864 A | 7/2000 | Buckner et al. |
| 6,093,186 A | 7/2000 | Goble |
| 6,102,497 A | 8/2000 | Ehr et al. |
| 6,102,907 A | 8/2000 | Smethers et al. |
| 6,104,248 A | 8/2000 | Carver |
| 6,106,524 A | 8/2000 | Eggers et al. |
| 6,113,591 A | 9/2000 | Whayne et al. |
| 6,113,592 A | 9/2000 | Taylor |
| 6,113,593 A | 9/2000 | Tu et al. |

(56) References Cited

U.S. PATENT DOCUMENTS

| | | | |
|---|---|---|---|
| 6,113,596 A | 9/2000 | Hooven et al. |
| 6,123,701 A | 9/2000 | Nezhat |
| 6,132,429 A | 10/2000 | Baker |
| 6,139,349 A | 10/2000 | Wright |
| 6,144,937 A | 11/2000 | Ali |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,173,713 B1 | 1/2001 | Dawson |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,238,387 B1 | 5/2001 | Miller |
| 6,238,388 B1 | 5/2001 | Ellman et al. |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu et al. |
| 6,246,912 B1 | 6/2001 | Cosman et al. |
| 6,251,106 B1 | 6/2001 | Becker et al. |
| 6,254,422 B1 | 7/2001 | Feye-Hohmann |
| 6,259,937 B1 | 7/2001 | Schulman et al. |
| 6,261,285 B1 | 7/2001 | Novak et al. |
| 6,267,760 B1 | 7/2001 | Swanson |
| 6,270,497 B1 | 8/2001 | Sekino et al. |
| 6,273,886 B1 | 8/2001 | Edwards et al. |
| 6,275,786 B1 | 8/2001 | Daners |
| 6,287,304 B1 | 9/2001 | Eggers et al. |
| 6,296,636 B1 | 10/2001 | Cheng et al. |
| 6,304,138 B1 | 10/2001 | Johnson |
| 6,306,131 B1 | 10/2001 | Hareyama et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,341,981 B1 | 1/2002 | Gorman |
| 6,350,262 B1 | 2/2002 | Ashley |
| 6,350,263 B1 | 2/2002 | Wetzig et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,387,092 B1 | 5/2002 | Burnside et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,424,186 B1 | 7/2002 | Quimby et al. |
| 6,426,886 B1 | 7/2002 | Goder |
| 6,427,089 B1 | 7/2002 | Knowlton |
| 6,428,537 B1 | 8/2002 | Swanson et al. |
| 6,440,157 B1 | 8/2002 | Shigezawa et al. |
| 6,451,015 B1 | 9/2002 | Rittman et al. |
| 6,454,594 B2 | 9/2002 | Sawayanagi |
| 6,458,121 B1 | 10/2002 | Rosenstock et al. |
| 6,458,122 B1 | 10/2002 | Pozzato |
| 6,464,689 B1 | 10/2002 | Qin et al. |
| 6,464,696 B1 | 10/2002 | Oyama et al. |
| 6,468,270 B1 | 10/2002 | Hovda et al. |
| 6,468,273 B1 | 10/2002 | Leveen et al. |
| 6,469,481 B1 | 10/2002 | Tateishi |
| 6,482,201 B1 | 11/2002 | Olsen et al. |
| 6,485,487 B1 | 11/2002 | Sherman |
| 6,488,678 B1 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,511,476 B2 | 1/2003 | Hareyama |
| 6,514,251 B1 | 2/2003 | Ni et al. |
| 6,517,538 B1 | 2/2003 | Jacob et al. |
| 6,522,931 B2 | 2/2003 | Manker et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,620,189 B1 | 9/2003 | Machold et al. |
| 6,626,901 B1 | 9/2003 | Treat et al. |
| 6,629,973 B1 | 10/2003 | Waardell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,645,198 B1 | 11/2003 | Bommannan et al. |
| 6,651,669 B1 | 11/2003 | Burnside |
| 6,652,513 B2 | 11/2003 | Panescu et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,703 B2 | 2/2004 | Pearson et al. |
| 6,689,131 B2 | 2/2004 | McClurken |
| 6,693,782 B1 | 2/2004 | Lash |
| 6,696,844 B2 | 2/2004 | Wong et al. |
| 6,700,076 B2 | 3/2004 | Sun et al. |
| 6,723,091 B2 | 4/2004 | Goble et al. |
| 6,730,078 B2 | 5/2004 | Simpson et al. |
| 6,730,079 B2 | 5/2004 | Lovewell |
| 6,733,498 B2 | 5/2004 | Paton et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |

(56)        References Cited

U.S. PATENT DOCUMENTS

| 6,819,027 B2 | 11/2004 | Saraf |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,855,141 B2 | 2/2005 | Lovewell |
| 6,855,142 B2 | 2/2005 | Harano et al. |
| 6,864,686 B2 | 3/2005 | Novak et al. |
| 6,875,210 B2 | 4/2005 | Refior et al. |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,962,587 B2 | 11/2005 | Johnson et al. |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,997,935 B2 | 2/2006 | Anderson et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | De Ruijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van |
| 7,311,703 B2 | 12/2007 | Turovskiy et al. |
| 7,316,682 B2 | 1/2008 | Konesky |
| 7,317,954 B2 | 1/2008 | Mcgreevy |
| 7,317,955 B2 | 1/2008 | Mcgreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,402,754 B2 | 7/2008 | Kirwan et al. |
| D574,323 S | 8/2008 | Waaler |
| 7,407,502 B2 | 8/2008 | Strul et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,468,499 B2 | 12/2008 | Canini et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,517,351 B2 | 4/2009 | Culp et al. |
| 7,525,398 B2 | 4/2009 | Nishimura et al. |
| 7,568,619 B2 | 8/2009 | Todd et al. |
| 7,573,693 B2 | 8/2009 | Hornung |
| 7,582,084 B2 | 9/2009 | Swanson et al. |
| 7,621,041 B2 | 11/2009 | Banerji et al. |
| 7,648,499 B2 | 1/2010 | Orszulak et al. |
| 7,651,492 B2 | 1/2010 | Wham |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | Mcgreevy et al. |
| 7,731,717 B2 | 6/2010 | Odom et al. |
| 7,736,358 B2 | 6/2010 | Shores et al. |
| 7,736,359 B2 | 6/2010 | Mcpherson |
| 7,744,593 B2 | 6/2010 | Mihori |
| 7,749,217 B2 | 7/2010 | Podhajsky |
| 7,766,693 B2 | 8/2010 | Sartor et al. |

(56)     References Cited

U.S. PATENT DOCUMENTS

| 7,766,905 B2 | 8/2010 | Paterson et al. |
| 7,780,662 B2 | 8/2010 | Bahney |
| 7,780,764 B2 | 8/2010 | Baksh |
| 7,799,020 B2 | 9/2010 | Shores et al. |
| 7,799,026 B2 | 9/2010 | Schechter et al. |
| 7,863,841 B2 | 1/2011 | Menegoli et al. |
| 7,863,984 B1 | 1/2011 | Behnke |
| 7,864,129 B2 | 1/2011 | Konishi |
| 7,879,029 B2 | 2/2011 | Jimenez |
| 7,879,033 B2 | 2/2011 | Sartor et al. |
| 7,901,400 B2 | 3/2011 | Wham et al. |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,025,660 B2 | 9/2011 | Plaven et al. |
| 8,034,049 B2 | 10/2011 | Odom et al. |
| 8,038,676 B2 | 10/2011 | Fischer |
| 8,070,746 B2 | 12/2011 | Orton et al. |
| 8,083,735 B2 | 12/2011 | Morris |
| 8,104,596 B2 | 1/2012 | Kim et al. |
| 8,105,323 B2 | 1/2012 | Buysse et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,200,317 B2 | 6/2012 | Baxi et al. |
| 8,202,271 B2 | 6/2012 | Orszulak |
| 8,211,100 B2 | 7/2012 | Podhajsky et al. |
| 8,216,219 B2 | 7/2012 | Desinger et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,231,614 B2 | 7/2012 | Dunning et al. |
| 8,231,616 B2 | 7/2012 | Mcpherson et al. |
| 8,235,917 B2 | 8/2012 | Joseph et al. |
| 8,241,278 B2 | 8/2012 | Sartor |
| 8,248,075 B2 | 8/2012 | Brannan et al. |
| 8,257,349 B2 | 9/2012 | Orszulak |
| 8,257,350 B2 | 9/2012 | Marion |
| 8,287,528 B2 | 10/2012 | Wham et al. |
| 8,287,529 B2 | 10/2012 | Orszulak |
| 8,292,883 B2 | 10/2012 | Kabaya et al. |
| 8,303,337 B2 | 11/2012 | Ballard et al. |
| 8,303,580 B2 | 11/2012 | Wham et al. |
| 8,333,759 B2 | 12/2012 | Podhajsky |
| 8,346,370 B2 | 1/2013 | Haley et al. |
| 8,353,903 B2 | 1/2013 | Podhajsky |
| 8,353,905 B2 | 1/2013 | Jensen et al. |
| 8,377,053 B2 | 2/2013 | Orszulak |
| 8,377,054 B2 | 2/2013 | Gilbert |
| 8,382,751 B2 | 2/2013 | Gilbert et al. |
| 8,398,627 B2 | 3/2013 | Hosier |
| 8,403,924 B2 | 3/2013 | Behnke et al. |
| 8,409,186 B2 | 4/2013 | Behnke et al. |
| 8,454,590 B2 | 6/2013 | Smith |
| 8,460,284 B2 | 6/2013 | Aronow et al. |
| 8,469,956 B2 | 6/2013 | Mckenna et al. |
| 8,475,447 B2 | 7/2013 | Orszulak et al. |
| 8,485,993 B2 | 7/2013 | Orszulak et al. |
| 8,486,061 B2 | 7/2013 | Podhajsky |
| 8,512,232 B2 | 8/2013 | Rothberg et al. |
| 8,523,855 B2 | 9/2013 | Keppel |
| 8,540,709 B2 | 9/2013 | Allen |
| 8,542,019 B2 | 9/2013 | Brannan et al. |
| 8,784,418 B2 | 7/2014 | Romero |
| 9,226,767 B2 | 1/2016 | Stulen et al. |
| 9,332,987 B2 | 5/2016 | Leimbach et al. |
| 9,861,425 B2 | 1/2018 | Behnke |
| 10,406,690 B1 | 9/2019 | Blankespoor et al. |
| 10,573,713 B2 | 2/2020 | Wen et al. |
| 10,653,417 B2 | 5/2020 | Shelton et al. |
| 10,761,524 B2 | 9/2020 | Wallace |
| 11,242,458 B2 | 2/2022 | Takada et al. |
| 11,278,346 B2 | 3/2022 | Messerly et al. |
| 2002/0022836 A1 | 2/2002 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0097912 A1 | 5/2004 | Gonnering |
| 2004/0133189 A1 | 7/2004 | Sakurai |
| 2004/0193021 A1 | 9/2004 | Zdeblick et al. |
| 2005/0004634 A1 | 1/2005 | Ricart et al. |
| 2005/0021020 A1 | 1/2005 | Blaha |
| 2005/0109111 A1 | 5/2005 | Manlove et al. |
| 2005/0109935 A1 | 5/2005 | Manlove et al. |
| 2005/0131390 A1 | 6/2005 | Heinrich et al. |
| 2006/0079774 A1 | 4/2006 | Anderson |
| 2006/0111711 A1 | 5/2006 | Goble |
| 2006/0155270 A1 | 7/2006 | Hancock et al. |
| 2006/0161148 A1 | 7/2006 | Behnke |
| 2006/0191926 A1 | 8/2006 | Ray et al. |
| 2006/0224053 A1 | 10/2006 | Black et al. |
| 2006/0224152 A1 | 10/2006 | Behnke et al. |
| 2006/0291178 A1 | 12/2006 | Shih |
| 2007/0088413 A1 | 4/2007 | Weber et al. |
| 2007/0093801 A1 | 4/2007 | Behnke |
| 2007/0173802 A1 | 7/2007 | Keppel |
| 2007/0173805 A1 | 7/2007 | Weinberg et al. |
| 2007/0173811 A1 | 7/2007 | Couture et al. |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2008/0004619 A1 | 1/2008 | Malis et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0132893 A1 | 6/2008 | D'Amelio et al. |
| 2008/0147056 A1 | 6/2008 | Van et al. |
| 2008/0177199 A1 | 7/2008 | Podhajsky |
| 2008/0203997 A1 | 8/2008 | Kroeger et al. |
| 2008/0234574 A1 | 9/2008 | Hancock et al. |
| 2008/0262489 A1 | 10/2008 | Steinke |
| 2008/0281311 A1 | 11/2008 | Dunning et al. |
| 2008/0281316 A1 | 11/2008 | Carlton et al. |
| 2008/0287943 A1 | 11/2008 | Weber et al. |
| 2008/0319350 A1 | 12/2008 | Wallace et al. |
| 2008/0319442 A1 | 12/2008 | Unger et al. |
| 2009/0018536 A1 | 1/2009 | Behnke |
| 2009/0030477 A1 | 1/2009 | Jarrard |
| 2009/0146635 A1 | 6/2009 | Qiu et al. |
| 2009/0157071 A1 | 6/2009 | Wham et al. |
| 2009/0240244 A1 | 9/2009 | Malis et al. |
| 2009/0248006 A1 | 10/2009 | Paulus et al. |
| 2009/0248007 A1 | 10/2009 | Falkenstein et al. |
| 2009/0254077 A1 | 10/2009 | Craig |
| 2009/0292283 A1 | 11/2009 | Odom |
| 2010/0030210 A1 | 2/2010 | Paulus |
| 2010/0042093 A9 | 2/2010 | Wham et al. |
| 2010/0076424 A1 | 3/2010 | Carr |
| 2010/0082023 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094288 A1 | 4/2010 | Kerr |
| 2010/0168572 A1 | 7/2010 | Sliwa et al. |
| 2010/0168730 A1 | 7/2010 | Hancock et al. |
| 2010/0168741 A1 | 7/2010 | Sanai et al. |
| 2010/0217258 A1 | 8/2010 | Floume et al. |
| 2010/0268220 A1 | 10/2010 | Johnson et al. |
| 2011/0028963 A1 | 2/2011 | Gilbert |
| 2011/0054460 A1 | 3/2011 | Gilbert |
| 2011/0071516 A1 | 3/2011 | Gregg |
| 2011/0077631 A1 | 3/2011 | Keller |
| 2011/0077639 A1 | 3/2011 | Brannan et al. |
| 2011/0087213 A1 | 4/2011 | Messerly et al. |

(56)  References Cited

U.S. PATENT DOCUMENTS

| | | | |
|---|---|---|---|
| 2011/0112530 A1 | 5/2011 | Keller | |
| 2011/0115562 A1 | 5/2011 | Gilbert | |
| 2011/0144635 A1 | 6/2011 | Harper et al. | |
| 2011/0213355 A1 | 9/2011 | Behnke | |
| 2011/0301607 A1 | 12/2011 | Couture | |
| 2011/0319881 A1 | 12/2011 | Johnston | |
| 2012/0004703 A1 | 1/2012 | Deborski et al. | |
| 2012/0010610 A1 | 1/2012 | Keppel | |
| 2012/0028373 A1 | 2/2012 | Belen et al. | |
| 2012/0029515 A1 | 2/2012 | Couture | |
| 2012/0101491 A1 | 4/2012 | Blaha | |
| 2012/0123405 A1 | 5/2012 | Moua et al. | |
| 2012/0172866 A1 | 7/2012 | Behnke | |
| 2012/0220997 A1 | 8/2012 | Johnston | |
| 2012/0239020 A1 | 9/2012 | Cunningham | |
| 2012/0239025 A1 | 9/2012 | Smith | |
| 2012/0239026 A1 | 9/2012 | Orszulak et al. | |
| 2012/0265194 A1 | 10/2012 | Podhajsky | |
| 2012/0265195 A1 | 10/2012 | Gilbert | |
| 2012/0265196 A1* | 10/2012 | Turner | H01H 1/00 606/34 |
| 2012/0310241 A1 | 12/2012 | Orszulak | |
| 2013/0023867 A1 | 1/2013 | Collins | |
| 2013/0023870 A1 | 1/2013 | Collins | |
| 2013/0023871 A1 | 1/2013 | Collins | |
| 2013/0030432 A1 | 1/2013 | Garrison et al. | |
| 2013/0035679 A1 | 2/2013 | Orszulak | |
| 2013/0053840 A1 | 2/2013 | Krapohl et al. | |
| 2013/0066311 A1 | 3/2013 | Smith et al. | |
| 2013/0067725 A1 | 3/2013 | Behnke et al. | |
| 2013/0072920 A1 | 3/2013 | Behnke et al. | |
| 2013/0072921 A1 | 3/2013 | Behnke et al. | |
| 2013/0072922 A1 | 3/2013 | Behnke et al. | |
| 2013/0072923 A1 | 3/2013 | Behnke et al. | |
| 2013/0079763 A1 | 3/2013 | Heckel et al. | |
| 2013/0184699 A1 | 7/2013 | Behnke et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke et al. | |
| 2013/0345696 A1 | 12/2013 | Behnke et al. | |
| 2014/0002056 A1 | 1/2014 | Moul et al. | |
| 2014/0015535 A1 | 1/2014 | Lopez | |
| 2014/0025064 A1 | 1/2014 | Collins et al. | |
| 2014/0148803 A1 | 5/2014 | Taylor | |
| 2015/0088117 A1 | 3/2015 | Gilbert et al. | |
| 2015/0297286 A1 | 10/2015 | Boudreaux et al. | |
| 2016/0120601 A1 | 5/2016 | Boudreaux et al. | |
| 2016/0175031 A1* | 6/2016 | Boudreaux | A61B 18/1442 606/52 |
| 2017/0189095 A1 | 7/2017 | Danziger et al. | |
| 2019/0000533 A1* | 1/2019 | Messerly | A61B 18/1206 |
| 2019/0357969 A1 | 11/2019 | Boudreaux | |
| 2020/0106220 A1 | 4/2020 | Henderson et al. | |
| 2020/0107845 A1 | 4/2020 | Kabala et al. | |
| 2020/0397432 A1 | 12/2020 | Messerly et al. | |
| 2021/0236198 A1 | 8/2021 | Boudreaux | |
| 2022/0387093 A1 | 12/2022 | Johnston et al. | |

FOREIGN PATENT DOCUMENTS

| | | | |
|---|---|---|---|
| DE | 1099658 B | 2/1961 | |
| DE | 1139927 B | 11/1962 | |
| DE | 1149832 B | 6/1963 | |
| DE | 1439302 A1 | 1/1969 | |
| DE | 2439587 A1 | 2/1975 | |
| DE | 2455174 A1 | 5/1975 | |
| DE | 2407559 A1 | 8/1975 | |
| DE | 2540968 A1 | 3/1977 | |
| DE | 2820908 A1 | 11/1978 | |
| DE | 2803275 A1 | 8/1979 | |
| DE | 2823291 A1 | 11/1979 | |
| DE | 2946728 A1 | 5/1981 | |
| DE | 3143421 A1 | 5/1982 | |
| DE | 3045996 A1 | 7/1982 | |
| DE | 3510586 A1 | 10/1986 | |
| DE | 3904558 A1 | 8/1990 | |
| DE | 3942998 A1 | 7/1991 | |
| DE | 4206433 A1 | 9/1993 | |
| DE | 4339049 A1 | 5/1995 | |
| DE | 19506363 A1 | 8/1996 | |
| DE | 19717411 A1 | 11/1998 | |
| DE | 19848540 A1 | 5/2000 | |
| DE | 102008058737 A1 | 4/2010 | |
| EP | 0246350 A1 | 11/1987 | |
| EP | 0267403 A2 | 5/1988 | |
| EP | 0296777 A2 | 12/1988 | |
| EP | 0309942 A2 | 4/1989 | |
| EP | 0336742 A2 | 10/1989 | |
| EP | 0503200 A2 | 9/1992 | |
| EP | 0556705 A1 | 8/1993 | |
| EP | 0878169 A1 | 11/1998 | |
| EP | 0880220 A2 | 11/1998 | |
| EP | 0882955 A1 | 12/1998 | |
| EP | 1157667 A2 | 11/2001 | |
| EP | 1263181 A1 | 12/2002 | |
| EP | 1278007 A1 | 1/2003 | |
| EP | 1495712 A1 | 1/2005 | |
| EP | 1535581 A2 | 6/2005 | |
| EP | 1609430 A1 | 12/2005 | |
| EP | 1707143 A1 | 10/2006 | |
| EP | 1902681 A1 | 3/2008 | |
| EP | 1994904 A1 | 11/2008 | |
| EP | 2025297 A2 | 2/2009 | |
| EP | 2111812 A2 | 10/2009 | |
| EP | 2156800 A1 | 2/2010 | |
| EP | 2253286 A1 | 11/2010 | |
| EP | 2345454 A1 | 7/2011 | |
| EP | 3824828 A1 | 5/2021 | |
| FR | 1275415 A | 11/1961 | |
| FR | 1347865 A | 1/1964 | |
| FR | 2313708 A1 | 12/1976 | |
| FR | 2502935 A1 | 10/1982 | |
| FR | 2517953 A1 | 6/1983 | |
| FR | 2573301 A1 | 5/1986 | |
| GB | 607850 A | 9/1948 | |
| GB | 702510 A | 1/1954 | |
| GB | 855459 A | 11/1960 | |
| GB | 902775 A | 8/1962 | |
| GB | 1290304 A | 9/1972 | |
| GB | 2154881 A | 9/1985 | |
| GB | 2214430 A | 9/1989 | |
| GB | 2331247 A | 5/1999 | |
| GB | 2358934 A | 8/2001 | |
| GB | 2434872 A | 8/2007 | |
| GB | 2559373 A | 8/2018 | |
| JP | S635876 A | 1/1988 | |
| JP | 2002065690 A | 3/2002 | |
| JP | 2005185657 A | 7/2005 | |
| SU | 166452 | 11/1964 | |
| SU | 727201 A2 | 4/1980 | |
| WO | 9206642 A1 | 4/1992 | |
| WO | 9207622 A1 | 5/1992 | |
| WO | 9324066 A1 | 12/1993 | |
| WO | 9424949 A1 | 11/1994 | |
| WO | 9518575 A1 | 7/1995 | |
| WO | 9525471 A2 | 9/1995 | |
| WO | 9608794 A1 | 3/1996 | |
| WO | 9639086 A1 | 12/1996 | |
| WO | 9639088 A1 | 12/1996 | |
| WO | 9639914 A1 | 12/1996 | |
| WO | 9706855 A2 | 2/1997 | |
| WO | 9717029 A1 | 5/1997 | |
| WO | 9743971 A2 | 11/1997 | |
| WO | 0054683 A1 | 9/2000 | |
| WO | 0101847 A1 | 1/2001 | |
| WO | 0211634 A1 | 2/2002 | |

(56) References Cited

FOREIGN PATENT DOCUMENTS

| WO | 0232333 | A1 | 4/2002 |
|----|---------|----|--------|
| WO | 0245589 | A2 | 6/2002 |
| WO | 0247565 | A2 | 6/2002 |
| WO | 02088128 | A1 | 11/2002 |
| WO | 2005046496 | A1 | 5/2005 |
| WO | 2005060365 | A2 | 7/2005 |
| WO | 2005060849 | A1 | 7/2005 |
| WO | 2006050888 | A1 | 5/2006 |
| WO | 2006105121 | A2 | 10/2006 |
| WO | 2007055491 | A1 | 5/2007 |
| WO | 2007076924 | A2 | 7/2007 |
| WO | 2007105963 | A1 | 9/2007 |
| WO | 2008002517 | A1 | 1/2008 |
| WO | 2008003058 | A2 | 1/2008 |
| WO | 2008011575 | A1 | 1/2008 |
| WO | 2008043999 | A2 | 4/2008 |
| WO | 2008044000 | A1 | 4/2008 |
| WO | 2008044013 | A2 | 4/2008 |
| WO | 2008053532 | A1 | 5/2008 |
| WO | 2008071914 | A2 | 6/2008 |
| WO | 2008101356 | A1 | 8/2008 |
| WO | 2016069204 | A1 | 5/2016 |
| WO | 2017058617 | A2 | 4/2017 |
| WO | 2019224636 | A2 | 11/2019 |

OTHER PUBLICATIONS

Partial European Search Report dated Feb. 10, 2023 corresponding to counterpart Patent Application EP 22196234.3.

Extended EP Search Report for application No. 22196234.3 dated Jun. 15, 2023.

Behnke, "Application and Filing History for U.S. Appl. No. 14/283,604, filed May 21, 2014", (Copy Not Attached).

Coulson et al., "Application and Filing History for U.S. Appl. No. 14/255,051, filed Apr. 17, 2014", (Copy Not Attached).

"Electrosurgical Unit Analyzer ESU-2400 Series User Manual", Retrieved from: https://www.bcgroupintl.com/ESU_2400/Updates/ESU-2400_UM_Rev04.pdf, Apr. 1, 2002, p. 6, 11 and 73.

Extended European Search Report issued in corresponding application EP 22177409.4 dated Nov. 3, 2022, 8 pages.

Friedrichs et al., "Application and Filing History for U.S. Appl. No. 14/174,607, filed Feb. 6, 2014", (Copy Not Attached).

Friedrichs et al., "Application and Filing History for U.S. Appl. No. 14/267,066, filed May 1, 2014", (Copy Not Attached).

Gilbert et al., "Application and Filing History for U.S. Appl. No. 14/190,895, filed Feb. 26, 2014", (Copy Not Attached).

Gilbert et al., "Application and Filing History for U.S. Appl. No. 14/320,762, filed Jul. 1, 2014", (Copy Not Attached).

Gilbert et al., "Application and Filing History for U.S. Appl. No. 14/320,804, filed Jul. 1, 2014", (Copy Not Attached).

Gilbert, "Application and Filing History for U.S. Patent Application No. 14/100, 113, filed on Dec. 9, 2013", (Copy Not Attached).

Gilbert, "Application and Filing History for U.S. Appl. No. 14/147,294, filed Jan. 3, 2014", (Copy Not Attached).

Gilbert, "Application and Filing History for U.S. Appl. No. 14/147,312, filed Jan. 3, 2014", (Copy Not Attached).

Gilbert, "Application and Filing History for U.S. Appl. No. 14/262,219, filed Apr. 25, 2014", (Copy Not Attached).

Johnson et al., "Application and Filing History for U.S. Appl. No. 14/096,341, filed Dec. 4, 2013", (Copy Not Attached).

Johnson et al., "Application and Filing History for U.S. Appl. No. 14/174,551, filed Feb. 6, 2014", (Copy Not Attached).

Johnson et al., "Application and Filing History for U.S. Appl. No. 14/190,830, filed Feb. 26, 2014", (Copy Not Attached).

Johnson et al., "Application and Filing History for U.S. Appl. No. 14/098,859, filed Dec. 6, 2013", (Copy Not Attached).

Johnson, "Application and Filing History for U.S. Appl. No. 14/179,724, filed Feb. 13, 2014", (Copy Not Attached).

Kerr, "Application and Filing History for U.S. Appl. No. 14/268,187, filed on May 2, 2014", (Copy Not Attached).

"Kleppinger Bipolar Forceps & Bipolar Generator", Richard Wolf Medical Instruments Corp. Brochure, Jan. 1989, 3 pages.

Larson et al., "Application and Filing History for U.S. Appl. No. 14/180,965, filed Feb. 14, 2014", (Copy Not Attached).

Larson et al., "Application and Filing History for U.S. Appl. No. 14/181,114, filed on Feb. 14, 2014", (Copy Not Attached).

Mattmiller et al., "Application and Filing History for U.S. Appl. No. 14/168,296, filed Jan. 30, 2014", (Copy Not Attached).

Non-Final Office Action received for U.S. Appl. No. 17/742,516, mailed on Mar. 18, 2025, 16 pages.

"The O.R. Pro 300", Medtrex Brochure-Total Control at Full Speed, Sep. 1998, 1 page.

"Valleylab Electroshield Monitoring System", Valleylab Brochure, Nov. 1995, 2 pages.

Wham et al., "Application and Filing History for U.S. Appl. No. 10/761,524, filed Jan. 21, 2004", (Copy Not Attached).

Wham et al., "Application and Filing History for U.S. Appl. No. 14/182,797, filed Feb. 18, 2014", (Copy Not Attached).

Wham, "Application and Filing History for U.S. Appl. No. 14/297,771, filed Jun. 6, 2014", (Copy Not Attached).

Wham, "Application and Filing History for U.S. Appl. No. 14/297,812, filed Jun. 6, 2014", (Copy Not Attached).

Wham, "Application and Filing History for U.S. Appl. No. 14/297,890, filed Jun. 6, 2014", (Copy Not Attached).

Alexander et al., "Magnetic Resonance Image-directed Stereotactic Neurosurgery: Use of Image Fusion with Computerized Tomography to Enhance Spatial Accuracy", Journal of Neurosurgery, vol. 83, No. 2, 1995, pp. 271-276.

Anderson et al., "A Numerical Study of Rapid Heating for High Temperature Radio Frequency Hyperthermia", International Journal of Bio-Medical Computing, vol. 35, No. 4, May 1994, pp. 297-307.

Astrahan, "A Localized Current Field Hyperthermia System for use with 192-iridium Interstitial Implants", Medical Physics, vol. 9, No. 3, 1982, pp. 419-424.

Becker, "Application and Filing History for U.S. Appl. No. 11/242,458, filed Oct. 3, 2005", 27 pages.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Bergdahl et al., "Studies on Coagulation and the Development of an Automatic Computerized Bipolar Coagulator", Journal of Neurosurgery, vol. 75, Jul. 1991, pp. 148-151.

Burdette et al., "In Vivo Probe Measurement Technique for Determining Dielectric Properties at VHF Through Microwave Frequencies", IEEE Transactions on Microwave Theory and Techniques, vol. MTT-28, No. 4, Apr. 1980, pp. 414-427.

Chicharo et al., "A Sliding Goertzel Algorith", Signal Processing, vol. 52, No. 3, Aug. 1996, pp. 283-297.

Cosman et al., "Methods of Making Nervous System Lesions", Neurosurgery, vol. 111, 1984, pp. 2490-2499.

Cosman et al., "Radiofrequency Lesion Generation and Its Effect on Tissue Impedance", Applied Neurosurgery, vol. 51, 1988, pp. 230-242.

Cosman et al., "Theoretical Aspects of Radiofrequency Lesions in the Dorsal Root Entry Zone", Neurosurgery, vol. 15, No. 6, 1984, pp. 945-950.

Geddes et al., "The Measurement of Physiologic Events by Electrical Impedance", The American Journal of Medical Electronics, Jan.-Mar. 1964, pp. 16-27.

Goldberg et al., "Tissue Ablation with Radiofrequency: Effect of Probe Size, Gauge, Duration, and Temperature on Lesion Volume", Academic Radiology, vol. 2, No. 5, 1995, pp. 399-404.

Hadley et al., "Inexpensive Digital Thermometer for Measurements on Semiconductors", International Journal of Electronics, vol. 70, No. 6, Jun. 1, 1991, pp. 1155-1162.

Behnke, "Application and Filing History for U.S. Appl. No. 10/406,690, filed Apr. 3, 2003", 12 pages.

Momozaki et al., "Electrical Breakdown Experiments with Application to Alkali Metal Thermal-to- Electric Converters", Energy Conversion and Management, vol. 44, No. 6, Apr. 1, 2003, pp. 819-843.

(56) References Cited

OTHER PUBLICATIONS

Muller et al., "Extended Left Hemicolectomy Using the LigaSure Vessel Sealing System", Innovations That Work, Sep. 1999, 4 pages.
Ni et al., "A Signal Processing Method for the Coriolis Mass Flowmeter Based on a Normalized Lattice Notch Filter", Journal of Applied Sciences, vol. 23, No. 2, Mar. 2005, pp. 160-164 (with English Abstract).
Ogden, "Goertzel Alternative to the Fourier Transform", Electronics World, vol. 99, No. 9, Jun. 1993, pp. 485-487.
Prutchi et al., "Design and Development of Medical Electronic Instrumentation", John Wiley and Sons, Inc., 2005.
Sugita et al., "Bipolar Coagulator with Automatic Thermocontrol", Journal of Neurosurgery, vol. 41, No. 6, Dec. 1974, pp. 777-779.
Vällfors et al., "Automatically Controlled Bipolar Electrocoagulation -"COA-COMP"" Neurosurgical Review, vol. 7, No. 2-3, 1984, pp. 187-190.
Wald et al., "Accidental Burns", The Journal of the American Medical Association, vol. 217, No. 7, Aug. 16, 1971, pp. 916-921.
Wham, "Application and Filing History for U.S. Appl. No. 10/573,713, filed Mar. 28, 2006", 18 pages.
Zlatanovic, "Sensors in Diffusion Plasma Processing", Proceedings of International Conference on Microelectronics, vol. 2, Sep. 12-14, 1995, pp. 565-570.

* cited by examiner

| 0 = Switch Open | | |
| --- | --- | --- |
| 1 = Switch Closed | | |
| | | |
| Switch | | |
| Activation | Jaw Aperture | Instrument State |
| 0 | 0 | Activation Off, Jaw Open or on Thick Tissue |
| 0 | 1 | Activation Off, Jaw Closed or on Thin Tissue |
| 1 | 0 | Activation On, Jaw Open or on Thick Tissue |
| 1 | 1 | Activation On, Jaw Closed or on Thin Tissue |
| Note: A Footswitch can be Used to Activate RF in Either of the First Two Cases. | | |

FIG. 7

MULTIPLEXED HAND SWITCHES FOR USE WITH ELECTROSURGICAL GENERATORS

CROSS-REFERENCE TO RELATED APPLICATIONS

The present application claims the benefit of and priority to U.S. Provisional Patent Application Ser. No. 63/245,213, filed on Sep. 17, 2021, the entire content of which being hereby incorporated by reference.

FIELD

The present disclosure relates to systems and methods for controlling an electrosurgical generator. In particular, the present disclosure relates to controlling an electrosurgical generator using multiplexed switches disposed in an electrosurgical device, such that each of the switches is actuated by a corresponding movable component of the electrosurgical device providing the status of the components to the electrosurgical generator, which may then control output based on the status of the switches.

BACKGROUND

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Hand switches are currently used with monopolar electrosurgical pencils. Thus, there is a need to provide similar hand switch functionality in other electrosurgical devices, such as bipolar forceps.

SUMMARY

According to one embodiment of the present disclosure, an electrosurgical system is disclosed. The electrosurgical system includes an electrosurgical device including a pair of opposing jaw members movable between an open jaw position and a closed jaw position, a main switch, a button configured to actuate the main switch, and a secondary switch configured to actuate based on the thickness of the grasped tissue. The system also includes an electrosurgical generator coupled to the electrosurgical device, the electrosurgical generator is configured to generate an electrosurgical output in response to actuation of the main switch and the secondary switch.

Implementations of the above embodiment may include one or more of the following features. According to one aspect of the above embodiment, the main switch includes a hand switch and/or a footswitch. The secondary switch may be disposed on one jaw member of the pair of opposing jaw members and is actuated when the pair of opposing jaw members are in the closed jaw position. The electrosurgical device may include a lever that is movable between an open lever position and a closed lever position to move the pair of opposing jaw members between the open jaw position and the closed jaw position, respectively. The electrosurgical device may include a handle and the secondary switch may be disposed on the handle and is actuated by the lever being in the closed lever position. The electrosurgical device may further include a multiplexer circuit configured to output a voltage signal based on actuation of the main switch and the secondary switch. The electrosurgical generator may include a signal processor coupled to the multiplexer circuit, the signal processor configured to output an activation signal based on the voltage signal. The signal processor may be a voltage comparator or an analog-to-digital converter coupled to a digital processor. The electrosurgical generator may further include a controller coupled to signal processor, the controller may be configured to output a control signal in response to the activation signal. The electrosurgical generator may further include: a power supply configured to output a direct current; a radio frequency inverter coupled to the power supply and configured to generate the electrosurgical output by inverting the direct current. The controller may be further configured to output the control signal to the radio frequency inverter to generate the electrosurgical output.

BRIEF DESCRIPTION OF THE DRAWINGS

The present disclosure may be understood by reference to the accompanying drawings, when considered in conjunction with the subsequent, detailed description, in which:

FIG. 7 is a table illustrating a plurality of input signals from the voltage network of FIG. 6 according to the present disclosure.

DETAILED DESCRIPTION

Figure 1:
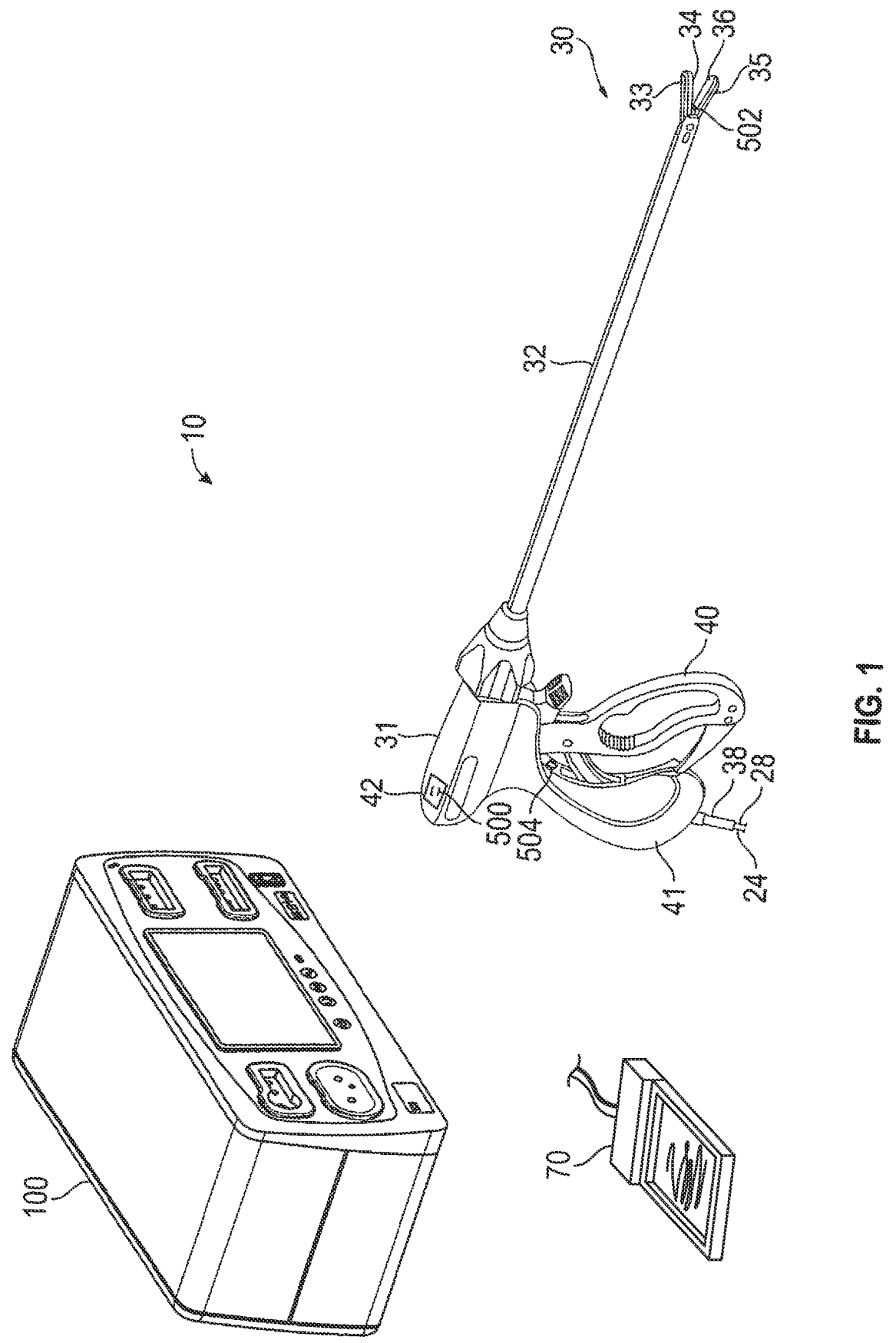
FIG. 1 is a perspective view of an electrosurgical system according to an embodiment of the present disclosure.

Embodiments of the presently disclosed system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 3:
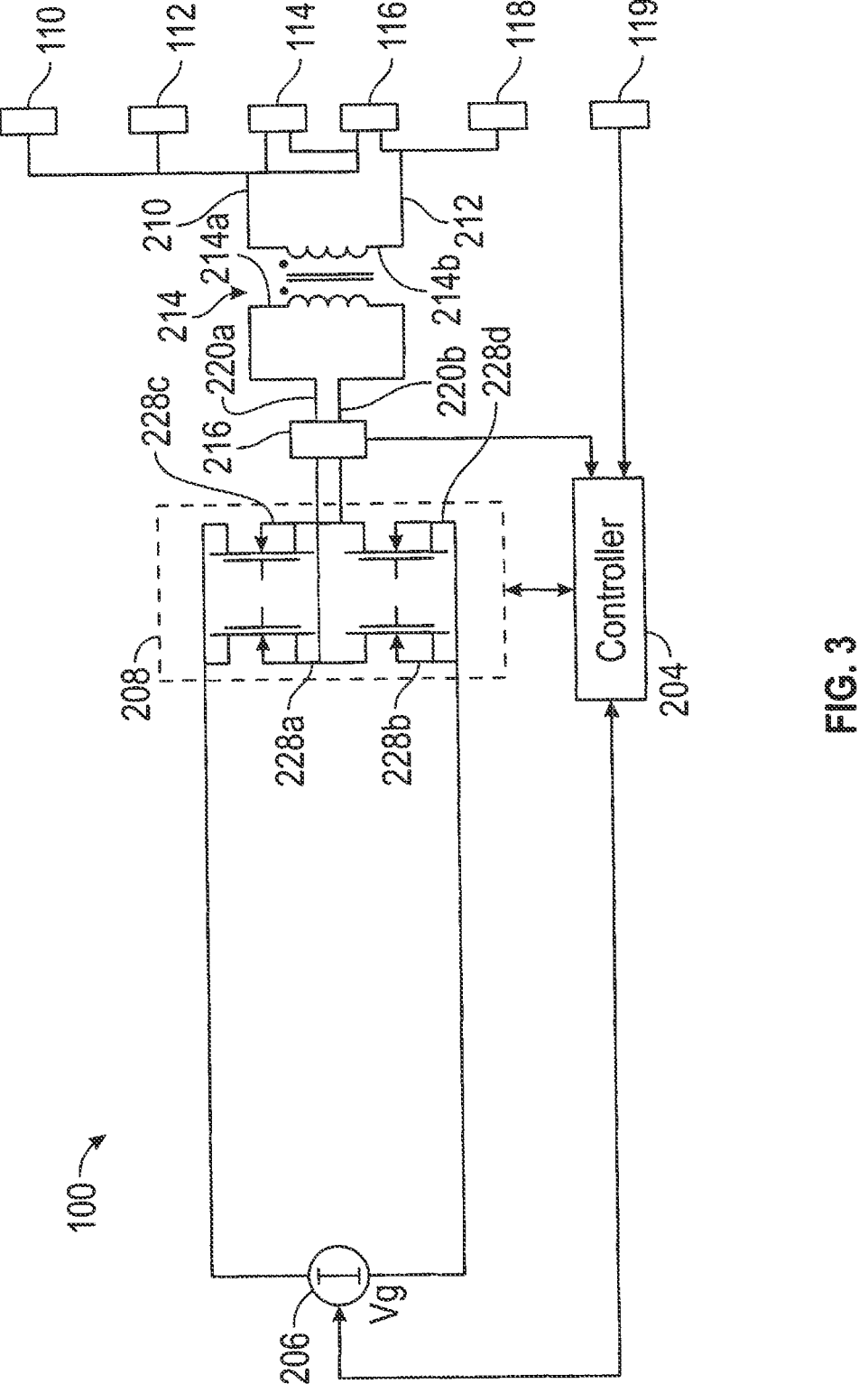
FIG. 3 is a schematic diagram of the electrosurgical generator of FIG. 1 according to an embodiment of the present disclosure.

Referring to FIG. 1 an electrosurgical system 10 is shown which includes one or more bipolar electrosurgical forceps 30 having electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 100 through cable 38 that includes the supply and return lines 24, 28, which may be coupled to the active and return terminals 210 and 212, respectively (FIG. 3). The electrosurgical forceps 30 is coupled to the generator 100 at a port having connections to the active and return terminals 210 and 212 (e.g., pins) via a plug disposed at the end of the cable 38, wherein the plug includes contacts from the supply and return lines 24, 28 as described in more detail below. The forceps 30 also includes a button 42 configured to signal to the generator 100 to output electrosurgical energy through the electrodes 34 and 36.

The forceps 30 also includes a lever 40 movable relative to a handle 41. The handle 41 is formed as part of the housing 31 and the lever 40 may be pivotably coupled within the housing 31. The lever 40 actuates, i.e., opens and closes, the jaw members 33 and 35, via one or more mechanical linkages. U.S. Pat. No. 8,784,418, titled "Endoscopic surgical forceps", provides additional disclosure of a bipolar electrosurgical forceps, the entire disclosure of which is incorporated by reference here. The lever 40 is movable from an open position (i.e., furthest distance from the handle 41) to a closed position (i.e., closest distance from the handle 41). The movement of the jaw members 33 and 35 corresponds to the movement of the lever 40. Thus, the jaw members are movable from an open position (i.e., furthest distance between the jaw members 33 and 35) to a closed position (i.e., closest between the jaw members 33 and 35, clamping tissue).

In addition, the electrosurgical system 10 also include a footswitch 70, which may be a pedal. The footswitch 70 may be paired to activate the forceps 30 and may provide an alternative activation mechanism in addition to the user inputs on the generator 100 or any hand switches present on instruments.

Figure 2:
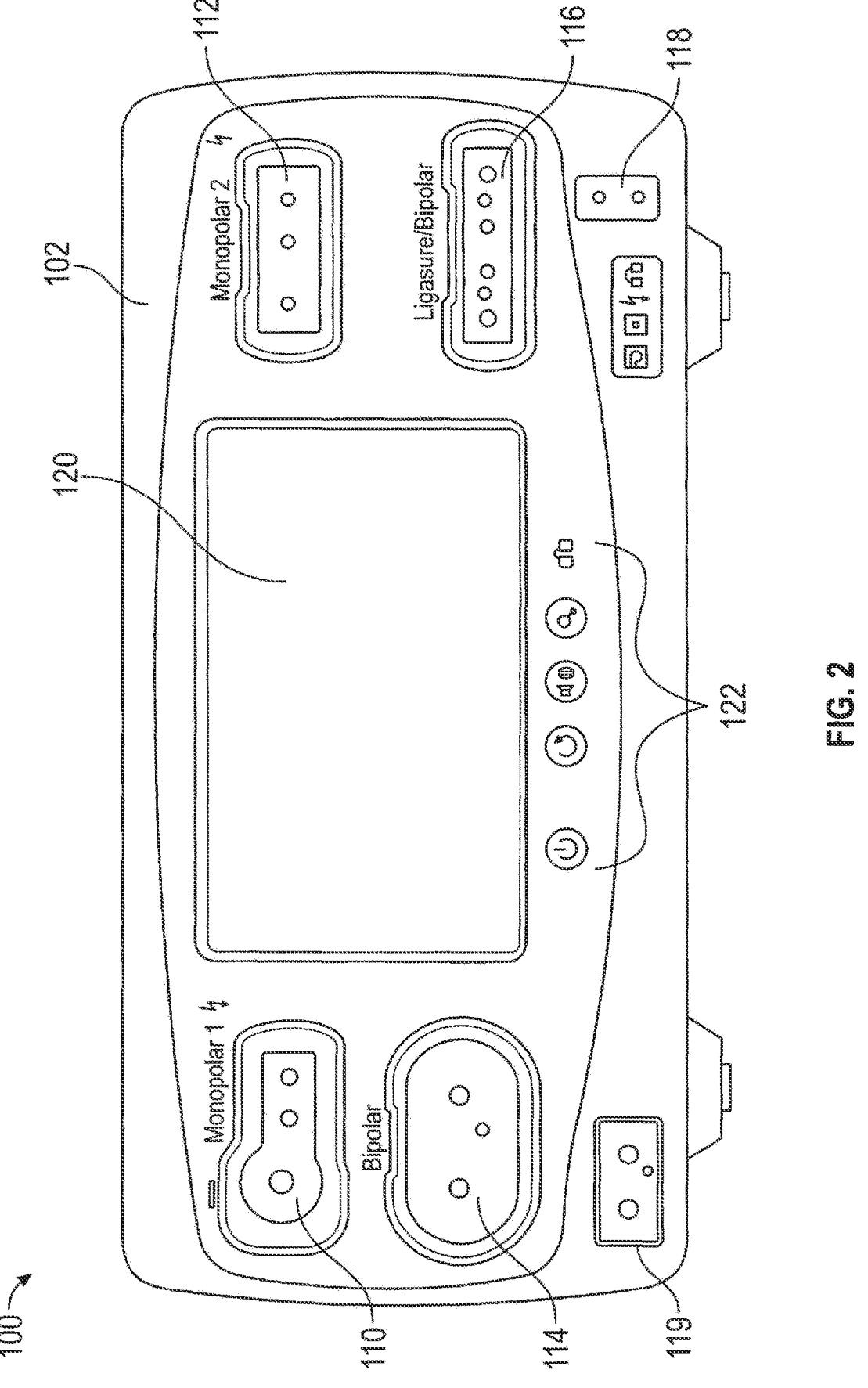
FIG. 2 is a front view of an electrosurgical generator of FIG. 1 according to an embodiment of the present disclosure.

With reference to FIG. 2, a front face 102 of the generator 100 is shown. The generator 100 may include a plurality of ports 110, 112, 114, 116 to accommodate various types of electrosurgical instruments and a port 118 for coupling to a return electrode pad and a port 119 configured to couple to a footswitch 70 (FIG. 1). The ports 110 and 112 are configured to couple to the monopolar electrosurgical instruments (e.g., first electrosurgical instrument). The ports 114 and 116 are configured to couple to bipolar electrosurgical instruments (e.g., second electrosurgical instrument). The generator 100 includes a display 120 for providing the user with variety of output information (e.g., intensity settings, treatment complete indicators, etc.). The display 120 is a touchscreen configured to display a menu corresponding to each of the ports 110, 112, 114, 116 and the instrument coupled. The user also adjusts inputs by touching corresponding menu options. The generator 100 also includes suitable input controls 122 (e.g., buttons, activators, switches, touch screen, etc.) for controlling the generator 100.

The generator 100 is configured to operate in a variety of modes and is configured to output monopolar and/or bipolar waveforms corresponding to the selected mode. Each of the modes may be activated by the button 42 disposed on the forceps 30. Each of the modes operates based on a preprogrammed power curve that limits how much power is output by the generator 100 at varying impedance ranges of the load (e.g., tissue). Each of the power curves includes power, voltage and current control ranges that are defined by the user-selected intensity setting and the measured impedance of the load.

The generator 100 may operate in the following monopolar modes, which include, but are not limited to, cut, blend, division with hemostasis, fulgurate and spray. The generator 100 may operate in the following bipolar modes, including bipolar cutting, bipolar coagulation, automatic bipolar which operates in response to sensing tissue contact, and various algorithm-controlled vessel sealing modes. The generator 100 may be configured to deliver energy required to power an ultrasonic transducer, thereby enabling control and modulation of ultrasonic surgical instruments.

Each of the RF waveforms may be either monopolar or bipolar RF waveforms, each of which may be continuous or discontinuous and may have a carrier frequency from about 200 kHz to about 500 kHz. As used herein, continuous waveforms are waveforms that have a 100% duty cycle. In embodiments, continuous waveforms are used to impart a cutting effect on tissue. Conversely, discontinuous waveforms are waveforms that have a non-continuous duty cycle, e.g., below 100%. In embodiments, discontinuous waveforms are used to provide coagulation effects to tissue.

With reference to FIG. 3, the generator 100 includes a controller 204, a power supply 206, and a RF inverter 208. The power supply 206 may be high voltage, DC power supplies connected to a common AC source (e.g., line voltage) and provide high voltage, DC power to their respective RF inverter 208, which then convert DC power into a RF waveform through active terminal 210 and return terminal 212 corresponding to the selected mode. The active terminal 210 and the return terminal 212 are coupled to the RF inverter 208 through an isolation transformer 214. The isolation transformer 214 includes a primary winding 214a coupled to the RF inverter 208 and a secondary winding 214b coupled to the active and return terminals 210 and 212.

RF energy for energizing a bipolar electrosurgical instrument, i.e., forceps 30, is delivered through the ports 114 and 116, each of which is coupled to the active terminal 210 and the return terminal 212. The generator 100 may include a plurality of steering relays or other switching devices configured to couple the active terminal 210 and the return terminals 212 to various ports 110, 112, 114, 116, 118 based on the combination of the electrosurgical instruments being used.

The RF inverter 208 is configured to operate in a plurality of modes, during which the generator 100 outputs corresponding waveforms having specific duty cycles, peak voltages, crest factors, etc. It is envisioned that in other embodiments, the generator 100 may be based on other types of suitable inverter topologies. RF inverter 208 may be a resonant RF amplifier or non-resonant RF amplifier, as shown. A non-resonant RF amplifier, as used herein, denotes an amplifier lacking any tuning components, i.e., inductors, capacitors, etc., disposed between the RF inverter and the load, e.g., tissue.

The controller 204 may include a processor (not shown) operably connected to a memory (not shown). The controller 204 is operably connected to the power supply 206 and/or RF inverter 208 allowing the processor to control the output of the RF inverter 208 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to the controller 204. The controller 204 then controls the power supply 206 and/or RF inverter 208, which adjust the DC and/or RF waveform, respectively.

The generator 100 according to the present disclosure may also include a plurality of sensors 216, each of which monitors output of the RF inverter 208 of the generator 100. The sensor 216 may be any suitable voltage, current, power, and impedance sensors. The sensors 216 are coupled to leads 220a and 220b of the RF inverter 208. The leads 220a and 220b couple the RF inverter 208 to the primary winding 214a of the transformer 214. Thus, the sensors 216 are configured to sense voltage, current, and other electrical properties of energy supplied to the active terminal 210 and the return terminal 212.

In further embodiments, the sensor 216 may be coupled to the power supply 206 and may be configured to sense properties of DC current supplied to the RF inverter 208. The controller 204 also receives input (e.g., activation) signals from the display 120, the input controls 122 of the generator 100 and/or the instrument (forceps 30). The controller 204 adjust power outputted by the generator 100 and/or perform other control functions thereon in response to the input signals.

The RF inverter 208 includes a plurality of switching elements 228a-228d, which are arranged in an H-bridge topology. In embodiments, RF inverter 208 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from silicon, gallium nitride, aluminum nitride, boron nitride, silicon carbide, or any other suitable wide bandgap materials.

The controller 204 is in communication with the RF inverter 208, and in particular, with the switching elements 228a-228d. Controller 204 is configured to output control signals, which may be pulse-width modulated ("PWM") signals, to switching elements 228a-228d. In particular, controller 204 is configured to modulate a control signal supplied to switching elements 228a-228d of the RF inverter 208. The control signal provides PWM signals that operate the RF inverter 208 at a selected carrier frequency. Additionally, controller 204 are configured to calculate power characteristics of output of the RF inverter 208 of the generator 100, and control the output of the generator 100 based at least in part on the measured power characteristics including, but not limited to, voltage, current, and power at the output of RF inverter 208. The RF inverter 208 may include transformer 214, and the power output may be measured at return terminals 210 and 212.

Figure 4:
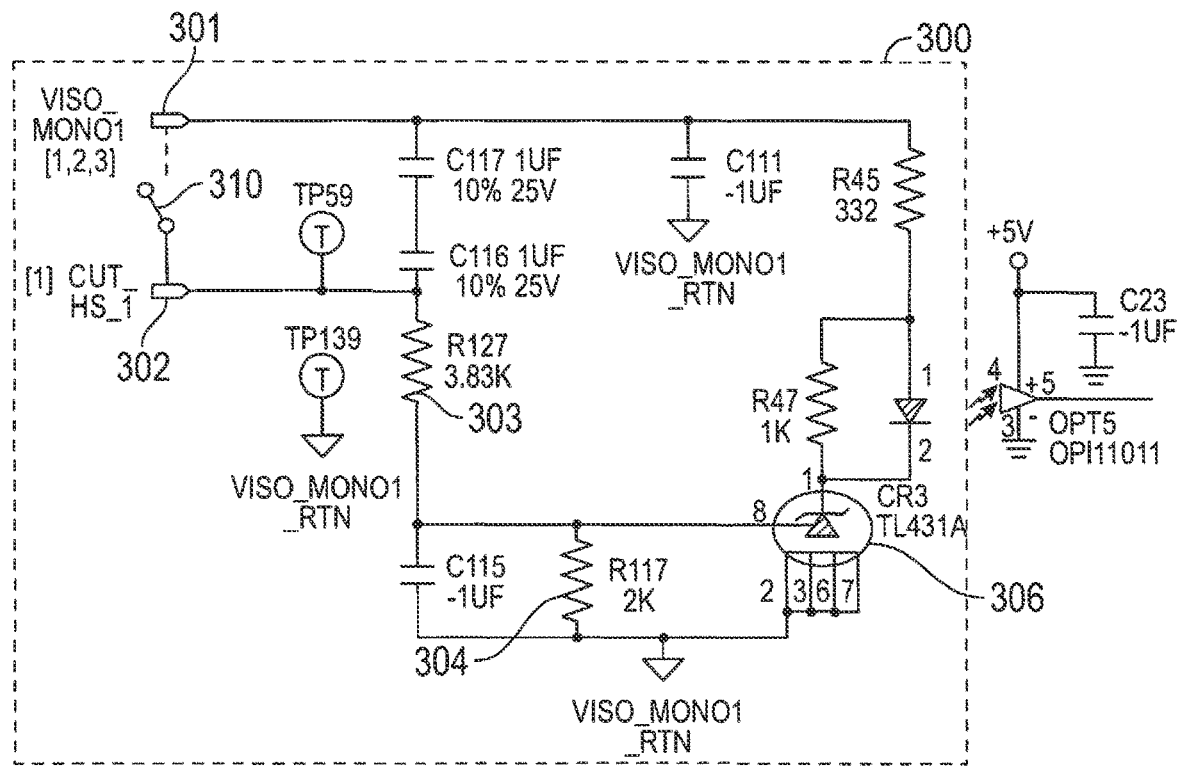
FIG. 4 is an electrical schematic diagram of a hand-switch detect circuit with a single input, according to one embodiment of the present disclosure.

The generator 100 is configured to receive switching signals from one or more switches disposed in the forceps 30, such as a switch that is actuated by the button 42, which is used to disable and enable output of the generator 100. With reference to FIG. 4, the generator 100 includes a detection circuit 300 having a first connection 301 and a second connection 302, which are coupled to a switch 310, which may be actuated by the button 42. The detection circuit 300 may be a resistor divider network and includes a first resistor 303 and a second resistor 304 having first and second resistances. The electrosurgical generator 100 includes a signal processor 306, which may be a voltage comparator, coupled to each of the first and second resistors 303 and 304 and is configured to output an activation signal based on the resistance of the detection circuit 300. Multiple switches can be electrically coupled to multiple resistors, such that different combinations of the resistors output different resistance values, which the signal processor 306 then outputs one of a plurality of control signals based on the resistance value. For example, signal processor 306 may act as a comparator and output two control signals, high and low.

Figure 5:
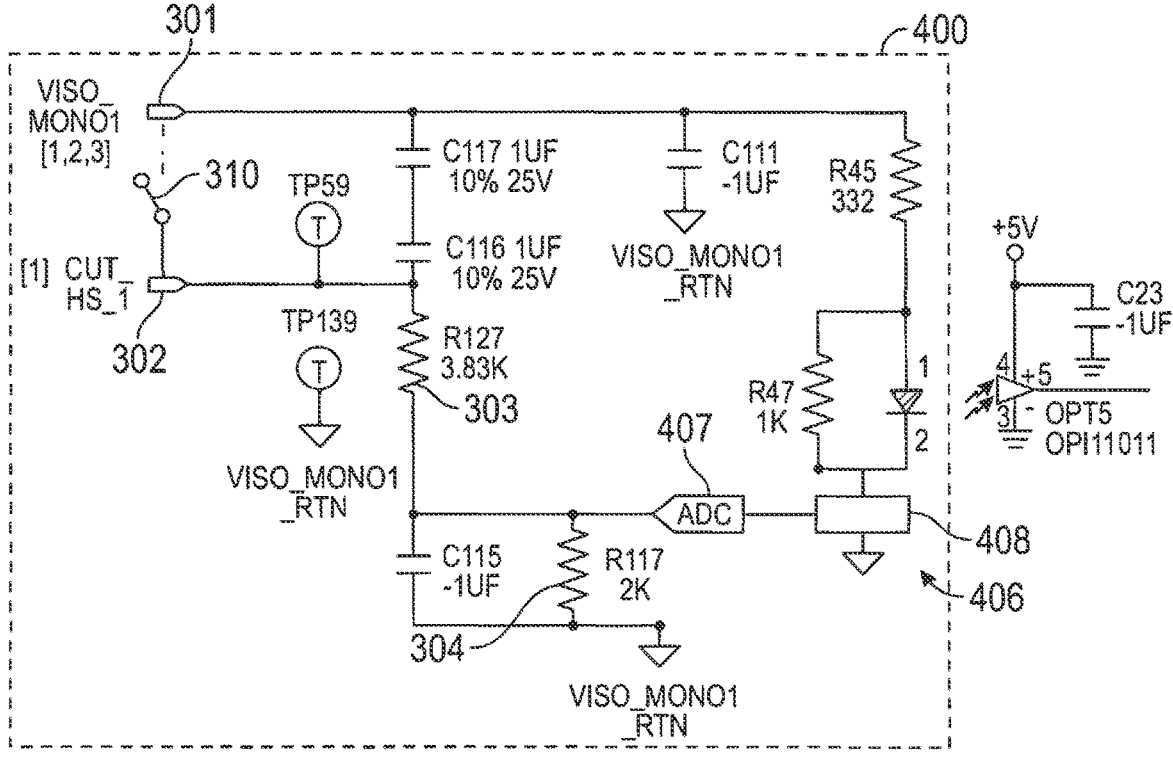
FIG. 5 is an electrical schematic diagram of a hand switch detect circuit with a single input, according to another embodiment of the present disclosure.

FIG. 5 shows another embodiment of a detection circuit 400, which is substantially similar to the detection circuit 300. The signal processor 306 of the electrosurgical generator 100 is replaced with a signal processor 406, which is a combination of an analog-to-digital converter (ADC) 407 and a digital processor 408, which provides more control over the voltage signals of the detection circuit 400. In embodiments, the digital processor 408 may be configured to adjust voltage thresholds, provide filtering, and detect hysteresis.

With reference to FIG. 1, the forceps 30 includes a plurality of switches, namely, a first (i.e., main) switch 500 and a second (i.e., secondary) switch 502. The first switch 500 is actuated by pressing of the button 42, which is used to activate the generator 100 to apply electrosurgical energy to the tissue grasped between the jaw members 33 and 35. The second switch 502 is coupled to one of the jaw members 33 and 35 and is actuated based on the position of the jaw members 33 and 35. In aspects, the second switch 502 may act as a tissue thickness sensor and may be actuated only when tissue grasped by jaw members 33 and 35 is above or below a predetermined thickness. The tissue thickness sensor may be a limit switch disposed on one of the jaw members 33 or 35 and actuated by the opposing jaw member 33 or 35.

Figure 6:
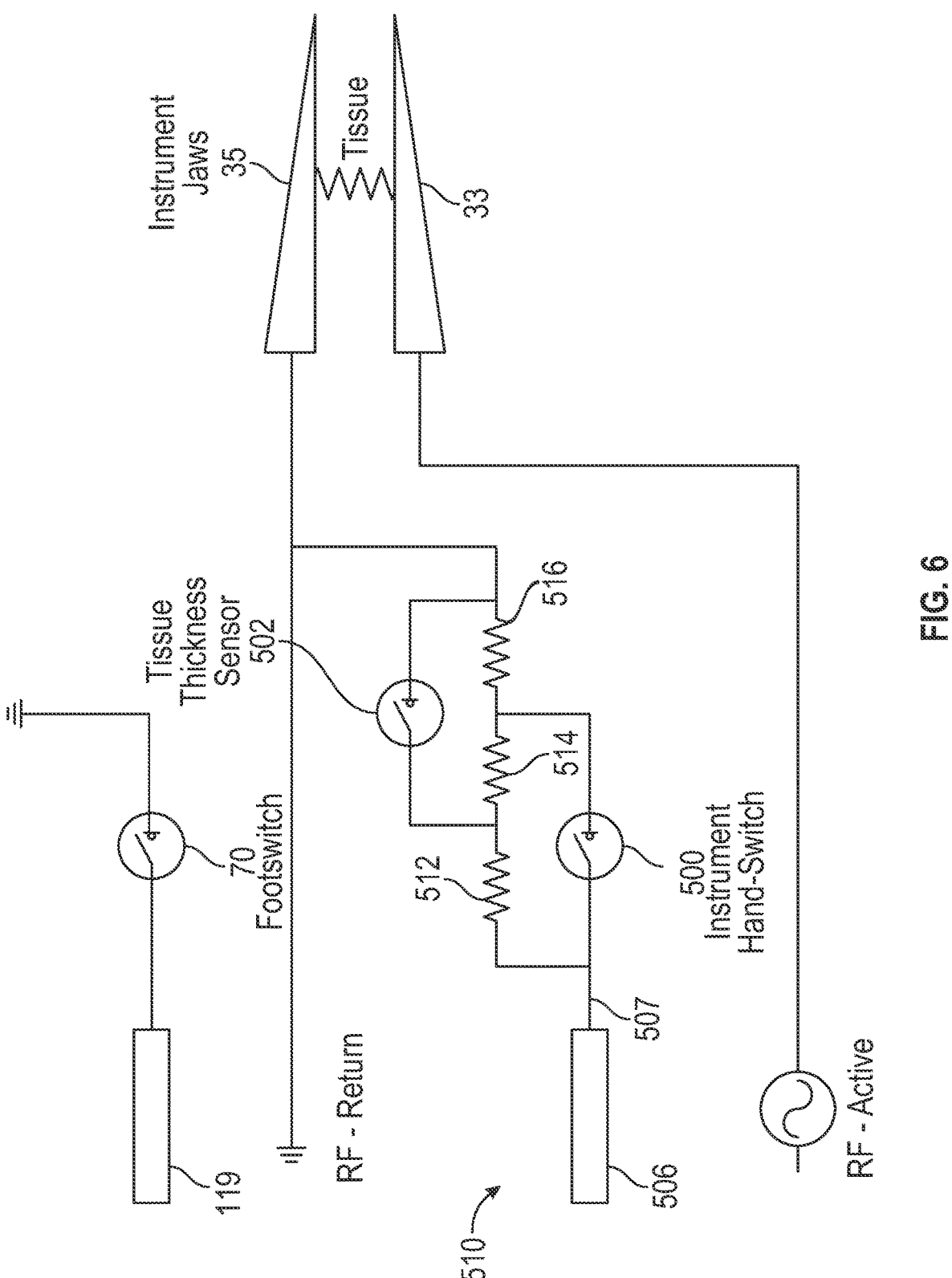
FIG. 6 is an electrical schematic diagram of a multiplexer circuit coupled to a plurality of switches disposed in an electrosurgical device of FIG. 1 according to one embodiment of the present disclosure.

With reference to FIG. 6, a multiplexer circuit 510 includes the first and second switches 500, and 502, coupled to a first resistor 512, second resistor 514, and third resistor 516. The multiplexer circuit 510 may be a resistor divider network and may be similar to the detection circuit 300 or the detection circuit 400 and includes a signal processor 506, which may be similar to either one of the signal processor 406. The multiplexer circuit 510 transmits switch inputs over a common transmission line 507, thereby acting as a multiplexer for multiple switch inputs. Activation of one or more of the first, and/or second switches 500, 502 outputs a unique voltage signal due to different combination of the first, second, and third resistors 512, 514, and 516 being included in the circuit of the multiplexer circuit 510. The first resistor 512 (e.g., about 2.2K ohms), second resistor 514 (e.g., about 287 ohms), and third resistor 516 (e.g., about 475 ohms) may have different values so that the multiplexer circuit 510 outputs four unique voltage signals based on the state of the first and second switches 500, 502, thus enabling the determination of the state (e.g., open/closed) of the first and/or second switch 500, 502 independently.

In embodiments, multiplexer circuit 510 may be configured to place the switch 500 such that the switch 500 may be open or closed while still enabling determination of the state of the switch 502. In aspects, a footswitch 70 (FIG. 1) coupled to port 119 of the generator 100 (FIG. 2) may be used to generate an activation signal while the first switch 500 is open, thus still enabling determination of the state of the second switch 502. Optionally, a third switch (not shown) may be actuated to detect lever position. An optional fourth resistor (not shown) would be used to enable the determination of the state of the third switch (not shown).

It is contemplated that more than two switches may be added to the multiplexer circuit 510 by adding additional resistors to the resistor divider network between the third resistor 516 and the return.

The unique voltage signal is processed by the signal processor 506 according to a truth table shown in FIG. 7. Accordingly, only when the signal processor 506 determines that a specific combination of the first and second switches 500, 502 is activated, the signal processor 506 outputs an activation signal to energize the generator 100 in a corresponding electrosurgical mode. Each of the first and second switches 500, 502 is activated in response to the actuation of the button 42, the handle 41 being in the closed position, and the jaw members 33 and 35 being in a position indicating that tissue above or below a predetermined thickness is grasped by jaw members 33 and 35. The truth table of FIG. 7 only shows the values for two switches, however, one of skill in the art would understand how to expand the truth table to incorporate any number of switches and resistors.

The electrosurgical generator 200 is configured to output energy according to one of a plurality of electrosurgical modes based on activation of a specific combination of the first and second switches 500, 502. If only the button 42 is pressed and the first switch 500 is activated, the electrosurgical generator 200 outputs energy in a first electrosurgical mode, e.g., cutting or coagulation. If all of the first and second switches 500, 502 are activated, the electrosurgical generator 200 determines that the jaws 33 and 35 are grasping tissue, the lever 40 is closed, and the button 42 is pressed, indicating to the electrosurgical generator 200 to output energy according to a second electrosurgical output, e.g., a tissue sealing algorithm. Thus, to seal tissue, the forceps 30 is not energized until both of the switches 500, 502, are closed (i.e., conditions are met). Once the signal processor 506 determines that one of the suitable combinations of the switches 500, 502, and/or footswitch 70 has been activated, the controller 204 then receives the activation signal from the signal processor 506 and controls the power supply 206 and the RF inverter 208 to output electrosurgical energy according to a corresponding electrosurgical mode.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical system comprising:
an electrosurgical device including:
    a pair of opposing jaw members movable between an open jaw position and a closed jaw position and configured to treat tissue;
    a foot switch configured to activate a supply of electrosurgical energy; and
    a multiplexer circuit for outputting a voltage signal, the multiplexer circuit comprising:
        a main switch configured to activate the supply of electrosurgical energy;
        a secondary switch configured to actuate based on a thickness of tissue grasped between the pair of opposing jaws; and
        one or more resistors coupled to the main switch and the secondary switch to at least partially define the voltage signal; and
        a signal processor configured to determine, based on the voltage signal, a switch combination comprising a switch state for each of the main switch and the secondary switch; and
an electrosurgical generator coupled to the electrosurgical device, the electrosurgical generator configured to generate an electrosurgical output in response to the switch combination.

2. The electrosurgical system according to claim 1, wherein the secondary switch is disposed on one jaw member of the pair of opposing jaw members and is actuated when the pair of opposing jaw members are in the closed jaw position.

3. The electrosurgical system according to claim 1, wherein the electrosurgical device includes a lever that is movable between an open lever position and a closed lever position to move the pair of opposing jaw members between the open jaw position and the closed jaw position, respectively.

4. The electrosurgical system according to claim 3, wherein the electrosurgical device includes a handle and the secondary switch is disposed on the handle and is actuated by the lever being in the closed lever position.

5. The electrosurgical system according to claim 1, wherein the signal processor is further configured to output an activation signal for the electrosurgical generator based on the voltage signal.

6. The electrosurgical system according to claim 5, wherein the signal processor includes a voltage comparator.

7. The electrosurgical system according to claim 5, wherein the signal processor includes an analog-to-digital converter and a digital processor configured to process an output signal from the converter.

8. The electrosurgical system according to claim 5, wherein the electrosurgical generator further includes a controller coupled to the signal processor, the controller configured to output a control signal in response to the activation signal.

9. The electrosurgical system according to claim 8, wherein the electrosurgical generator further includes:
    a power supply configured to output a direct current; and
    a radio frequency inverter coupled to the power supply and configured to generate the electrosurgical output by inverting the direct current.

10. The electrosurgical system according to claim 9, wherein the controller is further configured to output the control signal to the radio frequency inverter to generate the electrosurgical output.

* * * * *